United States Patent [19]
Monflier et al.

[11] Patent Number: 5,847,228
[45] Date of Patent: Dec. 8, 1998

[54] PROCESS FOR THE HYDROFORMYLATION OF AN OLEFIN IN A TWO-PHASE MEDIUM

[75] Inventors: Eric Monflier, Lille; André Mortreux; Yves Castanet, both of Hem, all of France

[73] Assignee: Centre National de la Recherche Scientifique, Paris, France

[21] Appl. No.: 875,080

[22] PCT Filed: Jan. 16, 1996

[86] PCT No.: PCT/FR96/00069

§ 371 Date: Jul. 17, 1997

§ 102(e) Date: Jul. 17, 1997

[87] PCT Pub. No.: WO96/22267

PCT Pub. Date: Jul. 25, 1996

[30] Foreign Application Priority Data

Jan. 17, 1995 [FR] France ................... 95 00466

[51] Int. Cl.⁶ .............................. C07C 45/50
[52] U.S. Cl. ........................... 568/454; 568/451
[58] Field of Search ................... 568/451, 454

[56] References Cited

U.S. PATENT DOCUMENTS 4,399,312  8/1983  Russell et al. .
5,091,350  2/1992  Cornils et al. .

FOREIGN PATENT DOCUMENTS 0157316  10/1985  European Pat. Off. .
2489308   9/1981  France .

OTHER PUBLICATIONS

Angewandte Chemie. International Edition, vol. 34, No. 20, Nov. 3, 1995, pp. 2269–2271, Monflier et al., "Molecular Recognition Between Chemically Modified Beta–Cyclodextrin and Dec–1–Ene: new Prospects for Biphasic Hydroformylation of Water–Insoluble Olefins".

Tetrahedron Letters, vol. 36, No. 52, pp. 9481–9484, Monflier et al., "A further Breathrough in Biphasic Rhodium–Catalyzed Hydroformylation: Use of per(2,6–di–O–methyl)–.beta.–cyclodextrin as Inverse Phase Transfer Catalyst" (1995).

Catalysis Letters, 9 (1991) 55–58, Anderson, et al., Hydroformylation of Olefins with Water–Soluble Rhodium Catalysts in the Presence of α–Cyclodextrin.

Angewandte Chemie. International Edition, vol. 33, No. 20, pp. 2100–2102, Monflier, et al.,; "Wacker Oxidation of 1–Decene to 2–Decanone in the Presence of a Chemcially Modified Cyclodextrin System: a Happy Union of Host—Guest Chemistry and Homogenous Catalysis" (1994).

*Primary Examiner*—Brian M. Burn
*Assistant Examiner*—Sreenivas Padmanabhan
*Attorney, Agent, or Firm*—Burns, Doane, Swecker & Mathis, L.L.P.

[57] ABSTRACT

The invention relates to a process for the hydroformylation of an olefin chosen from the alkenes represented by the formula $CnH_{2n}$ in which n is an integer less than or equal to 30, or chosen from functionalized olefins, by a $CO/H_2$ gas mixture in a two-phase medium, this process consisting in placing in contact, on the one hand, an aqueous solution containing a catalytic system consisting of a water-soluble transition metal complex and a water-soluble phosphine, and, on the other hand, an olefin, in heating the reaction mixture obtained with stirring, after it has been placed under a pressure of the $CO/H_2$ gas mixture, in which process a modified cyclodextrin is introduced into the aqueous solution containing the catalytic system.

37 Claims, No Drawings

PROCESS FOR THE HYDROFORMYLATION OF AN OLEFIN IN A TWO-PHASE MEDIUM

BACKGROUND OF THE INVENTION (i) Field of the Invention

This is the U.S. National Stage Application of PCT/FR96/00069 filed Jan. 16, 1996 now WO 96/22267 published Jul. 25, 1996.

The present invention relates to a process for the hydroformylation of an olefin.

(ii) Description of Related Art

It is known that the hydroformylation of olefins may be carried out in a homogeneous medium in the presence of solvents, in very good yield. However, the addition of solvents complicates the process, in particular in the case of olefins of high molar mass. The reason for this is that, in such a medium, the aldehydes can only be separated from the catalyst by distillation of the crude reaction mixture. In the case of heavy olefins, given the boiling points of the olefins and of the products formed, this distillation must be carried out at high temperatures, which causes, in the medium or long term, considerable degradation of the catalyst, which is economically unacceptable in particular when the catalyst is based on noble metals (Rh, Pt, etc).

To overcome this drawback, the hydroformylation of higher olefins has been carried out with $CO/H_2$ in a two-phase medium. The aim was to allow the ready separation of the catalyst (found in one phase) from the products obtained (which are in the other phase) by carrying out a simple separation by settling. Two main types of two-phase systems have been described: the water/organic phase system (the more common) and, more recently, the perfluoroalkane/organic phase system.

Various solutions have been proposed to dissolve the catalyst in perfluoroalkanes or in water, these consisting essentially in using fluorophosphines in the first case and water-soluble phosphines in the second case.

Thus, I. T. Horvath et al., (Science 1994 Vol. 266, 72) describe the hydroformylation of 1-decene dissolved in toluene, catalyzed by the complex HRh(CO) $[P\{CH_2CH_2(CF_2)_5CF_3\}]_3$ which is dissolved in $C_6F_{11}CF_3$ and in the presence of $P\{CH_2CH_2(CF_2)_5CF_3\}_3$. In this process, the catalyst is easily recycled since it is found in the perfluoro phase, whereas the aldehyde is in the toluene phase, which is immiscible with the former. However, the main difficulty lies in the synthesis of the very specific phosphine used. Moreover, the amount of rhodium present in the toluene phase is not specified.

The use of water/organic phase two-phase systems is much more common. Thus, E. Kuntz (Rhône-Poulenc) has proposed using triphenylphosphine trisulfonate (TPPTS) to dissolve metal complexes in water. This technique has been carried out industrially, in particular to perform the hydroformylation of propene into butanal with catalytic systems based on rhodium and TPPTS in aqueous solution (see for example Angewandte Chemie, Int. Ed. Eng. 1993, 1524–1544).

Admittedly, the use of a water-soluble phosphine does improve the hydroformylation process, but only in the case of light olefins that are partially soluble in an aqueous medium, the yield being very low with fatty olefins.

Thus, various studies have been targeted toward increasing the solubility of fatty olefins in an aqueous phase so as to be able to apply the two-phase process to them. The solutions proposed consisted mainly in adding a surfactant to the reaction medium containing a rhodium complex, a water-soluble phosphine and the olefin.

For example, in U.S. Pat. No. 4,399,312, 1981, Russel describes the use of dodecyltrimethylammonium bromide as surfactant, the aim of which is to make a fatty olefin, 1-decene, soluble in an aqueous medium. However, the yield still remains modest. In WO 93/04029, the same catalytic system was used, but with the catalyst being recovered by filtration through a membrane, which makes it possible to achieve extremely low residual rhodium concentrations in the organic phase. Nevertheless, this technique complicates the recovery of the catalyst considerably.

Hanson et al., (J. Mol. Catal. 1994 Vol. 88 43–56), describes the use of sodium dodecylbenzenesulfonate in the presence of various water-soluble phosphines for the hydroformylation of octene. However, the yields of aldehyde did not exceed 80% for the phosphine of highest performance.

The use of ammonium salt or of phosphonium salt as surfactant for the hydroformylation of fatty olefins is described in EP-A-0,602,444 and EP-A-0,602,463. The use of a rhodium salt, TTPTS as water-soluble phosphine and sodium dodecyl sulfate as surfactant, in the presence of butanol in order to produce a microemulsion, is described in EP-380,154 (Eniricerche).

In all these processes, the introduction of a surfactant results in the formation of a stable emulsion which makes it very difficult, or even impossible, to separate the organic phase which contains the catalyst from the aqueous phase which contains the aldehyde.

Moreover, cyclodextrins are cyclic oligomers of glucose that are α(1–4)-bridged. In this type of compound, the number of α-glucose units reaches 6, 7 and 8 for α-cyclodextrin, β-cyclodextrin and γ-cyclodextrin respectively. Their use in two-phase homogeneous catalysis reactions makes it possible to improve the speed and selectivity of certain reactions. Thus, H. Alper et al. has carried out the oxidation of olefins into ketones (J. Mol. Catal. 1986 Vol. 35 p. 249) using β-cyclodextrin as phase-transfer agent. The oxidation of alkenes into ketones in a two-phase medium, catalyzed by a system consisting of palladium/cyclodextrin has also been described by E. Monflier et al., (Angew. Chemie 1994, 106, 20, 2183). The authors have observed that the presence of a substituted or unsubstituted cyclodextrin improves the yield of the oxidation appreciably. The hydroformylation of olefins in the presence of α-cyclodextrin has been described by R. Anderson et al. (Catalysis Letters, 1991 Vol. 9 p. 55). Various transition metal complexes have been used as catalysts, in particular rhodium complexes, as well as various phosphines. The results obtained after comparative tests carried out in the presence of unmodified α-cyclodextrin led the authors to conclude that the addition of cyclodextrin to the reaction medium has an inhibitory effect on the hydroformylation of alkenes.

SUMMARY AND OBJECTS OF THE INVENTION

The present inventors have now found, surprisingly, that the use of a modified cyclodextrin in place of an unmodified cyclodextrin not only has no inhibitory effect on the hydroformylation reaction but also improves the yield of the hydroformylation substantially when compared with the process which does not use cyclodextrin.

Accordingly, the subject of the present invention is a process for the hydroformylation of an olefin chosen from the alkenes represented by the formula $C_nH_{2n}$ in which n is an integer less than or equal to 30, or chosen from functionalized olefins, by a $CO/H_2$ gas mixture in a two-phase medium, this process consisting in placing in contact, on the one hand, an aqueous solution containing a catalytic system consisting of a water-soluble transition metal complex and a water-soluble phosphine, and, on the other hand, an olefin, in heating the reaction mixture obtained with stirring, after it has been placed under a pressure of the $CO/H_2$ gas mixture, in which process a modified cyclodextrin is introduced into the aqueous solution containing the catalytic system.

DETAILED DESCRIPTION OF PREFERRED EMBODIMENTS

The alkenes which may be hydroformylated by the process of the invention may be linear or branched. Alkenes having from 8 to 20 carbon atoms are preferred, in particular linear alkenes having from 8 to 16 carbon atoms, more especially alkenes having a double bond in the end position. Examples of such alkenes which may be mentioned are 1-heptene, 1-octene, 1-nonene, 1-decene, 1-undecene, 1-dodecene, 1-tridecene and 1-tetradecene.

In the present text, the term functionalized olefin denotes a linear or branched alkene having a bulk which is less than the entry diameter of the cyclodextrin used and in which at least one of the carbon atoms of the ethylenic double bond bears at least one substituent chosen from:

saturated or unsaturated alicyclic radicals, preferably those which have from 6 to 30 carbon atoms;

linear or branched alkenyl radicals, preferably those which have from 2 to 30 carbon atoms;

aromatic radicals comprising one or more non-condensed aromatic rings which may be unsubstituted or substituted with an alkyl radical (preferably having not more than three carbon atoms) or with a functional group such as, for example, an ester function, a nitrile function, a ketone function, an acetal function or a hydroxyl function;

aromatic radicals comprising one or more condensed aromatic rings, which may be unsubstituted or substituted with an alkyl radical (preferably having not more than three carbon atoms) or with a functional group such as, for example, an ester function, a nitrile function, a ketone function, an acetal function or a hydroxyl function, preferably naphthyl radicals optionally bearing one or more alkyl substituents having from 1 to 3 carbon atoms;

alkyl radicals bearing an aryl substituent or a functional group such as, for example, an ester function, a nitrile function, a ketone function, an acetal function or a hydroxyl function;

ester functions and acyloxy functions.

Among the functionalized olefins, those in which the carbon-carbon double bond bears at least one hydrogen atom, and more especially at least two hydrogen atoms, are preferred. Functionalized olefins in which the carbon-carbon double bond bears three hydrogen atoms are particularly preferred.

The process may be carried out for an olefin having a single double bond, which may or may not be in the end position, or for an olefin having several double bonds. The process makes it possible to hydroformylate a single olefin or a mixture of different olefins.

The process of the present invention is particularly advantageous for the hydroformylation of a linear or branched alkene having from 2 to 30 carbon atoms, more especially for alkenes having from 8 to 30 carbon atoms, which cannot be hydroformylated in good yield by the processes of the prior art.

The catalyst used in the process of the present invention is a complex of a transition metal chosen from rhodium, ruthenium, palladium, iridium, cobalt, platinum, the platinum/tin couple and the platinum/iron couple, with a water-soluble phosphorus ligand. Rhodium complexes are particularly preferred. Non-limiting examples which may be mentioned are $Rh_6(CO)_{16}$, $Rh_4(CO)_{12}$, $HRhCO(PR_3)_3$ and $RhCl(PR_3)_3$ (in which R represents an aryl sulfone group, preferably a phenyl sulfone group), $Rh(acac)(CO)_2$ (acac representing an acetylacetonate radical), $Rh_2Cl_2(CO)_4$, rhodium oxides $(Rh_2O_3)$ and rhodium salts such as $RhCl_3$ and $Rh(OAc)_3$.

The water-soluble phosphines correspond to the following general formula:

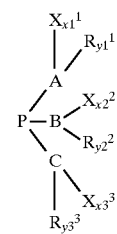

in which:

A, B and C, which may be identical or different, each represent an aryl group chosen from phenyl groups and naphthyl groups, or from alkyl groups having from 1 to 10 carbon atoms;

the substituents $R^1$, $R^2$ and $R^3$, which may be identical or different, each represent a group chosen from hydrogen, alkyl radicals having from 1 to 4 carbon atoms, alkoxy radicals having from 1 to 4 carbon atoms, halogen atoms, —CN, —$NO_2$, —OH and —$N(Z^1)(Z^2)$ groups, $Z^1$ and $Z^2$, which may be identical or different, each representing an alkyl radical having from 1 to 5 carbon atoms;

the substituents $X^1$, $X^2$ and $X^3$, which may be identical or different, each represent a carboxylic acid group, a sulfonic acid group or salts thereof. When $X^1$, $X^2$ or $X^3$ represents a carboxylic or sulfonic acid salt, the cation may be an alkali-metal or alkaline-earth metal cation or an ammonium cation of formula $N(T^1T^2T^3T^4)^+$ in which $T^1$, $T^2$, $T^3$ and $T^4$, which may be identical or different, each represent an alkyl group containing from 1 to 4 carbon atoms;

x1, x2 and x3 are identical or different numbers, ranging between 0 and 3 inclusive, at least one of them being greater than or equal to 1;

y1, y2 and y3 are identical or different numbers, ranging between 2 and 5 inclusive.

Preferably, A, B and C each represent an aryl group, more particularly a phenyl group; the substituents $X^1$ to $X^3$ are —$SO_3Na$ or —$CO_2Na$; the substituents $R^1$ to $R^3$ are hydrogen or an alkyl group; the numbers x1, x2 and x3 are equal to 1 or 0 (at least one of them being equal to 1); the numbers y1, y2 and y3 are equal to 4 or 5. Examples which may be mentioned are triphenylphosphine trisulfonate (TPPTS) (A=B=C=phenyl; $R^1$=$R^2$=$R^3$=H; $X^1$=$X^2$=$X^3$=$SO_3Na$; x1=x2=x3=1; y1=y2=y3=4), monosulfonated triphenylphosphine (TPPMS), monocarboxylic triphenylphosphine (TPPMC) and tricarboxylic triphenylphosphine (TPPTC). The phosphines which are particularly advantageous for the process of the present invention are TPPTS and TPPMS.

The present invention may also be carried out with a water-soluble diphosphine of general formula:

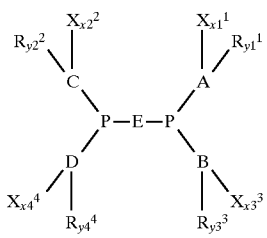

in which:

A, B, C and D, which may be identical or different, each represent an aryl group chosen from phenyl or naphthyl groups, and from alkyl groups having from 1 to 10 carbon atoms;

E represents a linear or branched alkyl chain containing from 1 to 10 carbon atoms or a chain containing one or more substituted or unsubstituted phenyl groups, or a cycloalkane optionally comprising linear or branched alkyl substituents having from 1 to 6 carbon atoms;

the substituents $R^1$, $R^2$, $R^3$ and $R^4$, which may be identical or different, each represent a group chosen from hydrogen, alkyl radicals having from 1 to 4 carbon atoms, alkoxy radicals having from 1 to 4 carbon atoms, halogen atoms, —CN, —NO$_2$, —OH and —N($Z^1$) ($Z^2$) groups, $Z^1$ and $Z^2$, which may be identical or different, each re-presenting an alkyl radical having from 1 to 5 carbon atoms;

the substituents $X^1$, $X^2$, $X^3$ and $X^4$ which may be identical or different, each represent a carboxylic acid group, a sulfonic acid group or salts thereof. When $X^1$, $X^2$, $X^3$ or $X^4$ represents a carboxylic or sulfonic acid salt, the cation may be an alkali-metal or alkaline-earth metal cation or an ammonium cation of formula $N(T^1T^2T^3T^4)^+$ in which $T^1$, $T^2$, $T^3$ and $T^4$, which may be identical or different, each represent an alkyl group containing from 1 to 4 carbon atoms;

x1, x2, x3 and x4 are identical or different numbers, ranging between 0 and 3 inclusive, at least one of them being greater than or equal to 1;

y1, y2, y3 and y4 are identical or different numbers, ranging between 2 and 5 inclusive.

Preferably, A, B, C and D are aryl groups, in particular a phenyl group; E is a linear alkyl chain containing 2 to 4 carbon atoms; the substituents $X^1$ to $X^4$ are —SO$_3$Na and —CO$_2$Na; the substituents $R^1$ to R4 are hydrogen or an alkyl group; the numbers x1 to x4 are equal to 1 or 0 (at least one of them being equal to 1); the numbers y1 to y4 are equal to 4 or 5. Examples which may be mentioned are 1,2-bis(diphenylphosphino)-ethane sulfonate and 1,3-bis(diphenylphosphino)propane sulfonate.

A modified cyclodextrin used in the process of the present invention is a cyclodextrin which bears one or more substituents, which may be identical or different, chosen from alkyl radicals which may or may not be functionalized, hydroxyalkyl radicals, carboxyl, carboxylates, nitro, amino, sulfonate, sulfate, phosphate, ether, polyether and ammonium radicals and radicals comprising an ester function. As alkyl radical, mention may be made of a linear or branched alkyl radical having from 1 to 20 carbon atoms, preferably from 1 to 5 carbon atoms, more particularly a methyl or ethyl radical. As hydroxyalkyl radical, mention may be made of a hydroxyalkyl group having from 1 to 20 carbon atoms, preferably 1 to 5 carbon atoms, more particularly a —CH$_2$CH$_2$OH or —CH$_2$OH radical. As radical containing an ester function, mention may be made of an ester group having from 1 to 20 carbon atoms, preferably 1 to 5 carbon atoms, more particularly the groups —O(CO)CH$_3$ and —O(CO)CH$_2$CH$_3$. The modified cyclodextrin may be a modified α-cyclodextrin (6 glucose units modified with an above substituent), the entry diameter of which is 4.9 Å, a modified β-cyclodextrin (7 modified glucose units) the entry diameter of which is 6.2 Å, or a modified γ-cyclodextrin (8 modified glucose units), the entry diameter of which is 7.9 Å. A mixture of two or more modified cyclodextrins mentioned above may moreover be used. The modified cyclodextrins may optionally be used in a form polymerized with epichlorohydrin, for example. Examples which may be mentioned are methylated, ethylated, propylated, succinylated, carboxylated, acetylated, 2-hydroxypropylated and polyoxyethylated cyclodextrins. A particularly advantageous cyclodextrin for the process of the present invention is dimethyl-β-cyclodextrin.

The modified cyclodextrin may be introduced into the aqueous solution containing the catalytic system before addition of the olefin. It may also be introduced into said solution after addition of the olefin.

In the reaction mixture, the phosphine/transition metal molar ratio is between 1 and 100, preferably between 2 and 20, more particularly equal to 5. The molar ratio of the modified cyclodextrin to the transition metal is between 1 and 100, preferably between 2 and 20, more particularly equal to 7.

The temperature and pressure conditions are those conventionally employed in the two-phase hydroformylation processes of the prior art. The temperature is advantageously between 20° C. and 200° C. The pressure is between 1 and 300 bar, preferably between 2 and 100 bar, the partial pressure of carbon monoxide being between 0.5 and 95 bar. In a conventional manner, synthesis gas may be used as a convenient source of carbon monoxide and hydrogen.

The reaction is carried out in the absence of solvent in order to facilitate recycling of the catalyst. At the end of the reaction, the catalyst is found in the aqueous phase and separation of the aqueous phase from the organic phase containing the aldehyde is easy. However, it is possible to add an organic solvent that is immiscible with the aqueous phase and/or a polar solvent that is immiscible with the organic phase, if necessary.

The present invention is described in greater detail in the examples given below, it being understood that the invention is not limited to the examples described.

Example 1

45 ml of an aqueous solution containing 0.8 mmol (426 mg) of TPPTS, 0.16 mmol (41 mg) of Rh(acac) (CO)$_2$ and 2.24 mmol of dimethyl-β-cyclo-dextrin were introduced into a 100 ml autoclave. The organic phase, consisting of 80 mmol of 1-decene, was then added. The autoclave was heated to 80° C., placed under a pressure of 50 bar with a CO/H$_2$ equimolar mixture and the stirring was brought to 1000 revolutions/minute. The pressure was kept constant with the aid of a ballast throughout the reaction. The conversion was monitored by taking samples. Chromatographic analysis of these samples (undecane used as internal standard) showed that the conversion was complete after 8 hours and that the selectivity towards hydroformylation products was 95%. The undecanal/2-methyldecanal molar ratio was 1.9. The initial activity of the catalyst (number of moles of 1-decene converted per mole of catalyst and per h) was 300 h$^{-1}$.

Examples 2 to 10

These examples were carried out under experimental conditions identical to those of Example 1, except where otherwise mentioned, with a cyclo-dextrin/rhodium ratio=7.

They show the influence of the nature of the group modifying the cyclodextrin and the phosphine/rhodium and cyclodextrin/rhodium ratios on the conversion and the selectivity. Example 2 is a comparative example without cyclodextrin and is given as a guide. Examples 9 and 10 show that the present invention may be carried out with other water-soluble phosphines such as triphenylphosphine monosulfonate (TPPMS).

The specific experimental conditions and the results obtained are collated in Table 1 below.

genated into fatty alcohols which have many applications in the chemical industry, in particular the synthesis of detergents or the preparation of plasticizers.

Examples 12 to 22

Examples 12 to 22 below illustrate the use of the process of the invention for various olefins under conditions similar to those of Example 1, with a dimethyl-β-cyclodextrin/rhodium ratio=14 and a TPPTS/Rh ratio=5.

The results obtained are given in Table 2 below, in which:

TABLE 1

| Example | Phosphine | Modified cyclodextrin[a] Modification | $R^1$ | $R^2$ | Reaction time (hours) | Conversion of the 1-decene[b] (mol %) | Hydroformylation selectivity[c] (mol %) | Linear/branched ratio[d] |
|---|---|---|---|---|---|---|---|---|
| 2[e] | TPPTS | | | | 8 | 10 | 64 | 2.7 |
| 3 | TPPTS | —CCH$_3$ | 14 | 7 | 8 | 76 | 91 | 1.8 |
| 4[f] | TPPTS | —OCH$_3$ | 14 | 7 | 8 | 100 | 95 | 1.9 |
| 5[g] | TPPTS | —OCH$_3$ | 14 | 7 | 6 | 94 | 75 | 2.0 |
| 6[h] | TPPTS | —OCH$_3$ | 14 | 7 | 8 | 32 | 99 | 2.1 |
| 7 | TPPTS | —OCH$_2$CH(OH)CH$_3$ | 0.22 | 15.4 | 8 | 32 | 84 | 2.0 |
| 8 | TPPTS | —O(CO)CH$_2$C(H)(R)(CO$_2$Na)[i] | 5.6 | 20.78 | 10 | 32 | 73 | 2.1 |
| 9 | TPPMS | —OCH$_3$ | 14 | 7 | 1.5 | 100 | 92 | 2.5 |
| 10 | TPPMS | —OCH$_3$ | 14 | 7 | 1.3 | 100 | 92 | 2.5 |

[a]: $R^1$ = number of modifying groups per β-cyclodextrin; $R^2$ = number of OH per β-cyclodextrin;
[b](number of moles of 1-decene converted/number of moles of 1-decene initially introduced) × 100;
[c](number of moles of undecanal and of 2-methyldecanal/number of moles of 1-decene converted) × 100;
[d]number of moles of undecanal/number of moles of 2-methyldecanal;
[e]comparative example;
[f]the cyclodextrin/rhodium ratio is 14;
[g]the phosphine/rhodium ratio is 2
[h]the phosphine/rhodium ratio is 15
[i]R=CH$_3$(CH$_2$)$_4$CH=CH—CH$_2$—

Example 11

45 ml of an aqueous solution containing 0.8 mmol of Co$_2$(CO)$_6$(TPPTS)$_2$ and 0.93 mmol of dimethyl-β-cyclodextrin (1.22 g) were introduced into a 100 ml autoclave. The organic phase, consisting of 80 mmol of 1-decene, was then added. The autoclave was heated to 160° C., placed under a pressure of 50 bar with an equimolar CO/H$_2$ mixture and the stirring was brought to 1000 revolutions/minute. The pressure was kept constant with the aid of a ballast throughout the reaction. The conversion was monitored by taking samples. Chromatographic analysis of these samples showed that the conversion was complete after 18 hours and that the selectivity towards hydroformylation products was 30%. The undecanal/2-methyldecanal molar ratio was 1.6.

In all these examples, the separation of the organic and aqueous phases is very easy. There is no formation of an emulsion and the separation is very rapid. Analysis of the organic phase obtained in Example 1 shows that the rhodium concentration therein is less than 0.5 ppm and that the phosphorus concentration is 1.4 ppm, which confirms the great value of the process. Thus, the hydroformylation process of the present invention is of great value since it makes it possible to obtain fatty aldehydes by readily recycling the catalyst without loss, thereby making it an economic process. The fatty aldehydes are generally hydrothe examples according to the invention are numbered from 12 to 22 respectively and the results obtained relating to the conversion (Conv.), the selectivity (Selec.) and the linear aldehyde/branched aldehyde (lin/bran) ratio are given;

each of the numbers indicated corresponding to the results obtained by the process of the invention is followed by a number in parentheses which corresponds to the result obtained by a comparative example performed under the same conditions as the example according to the invention, but without using dimethyl-β-cyclodextrin;

the duration, expressed in hours, is the time required to obtain the corresponding degree of conversion indicated;

the conversion represents the (number of moles of olefin introduced)/(number of moles of olefin converted) ratio;

the selectivity represents the (number of moles of aldehyde formed)/(number of moles of olefin converted) ratio;

the (linear aldehyde/branched aldehyde) ratio means, for Example 22, the β-aldehyde/α-aldehyde ratio. The γ-aldehyde is detected for comparative Example 22';

in Example 15, the internal double bond is not hydroformylated.

TABLE 2

| Example | Olefin | Duration | Conv. | Selec. | Lin./Branched |
|---|---|---|---|---|---|
| 12 | $C_{10}H_{21}CH=CH_2$ | 6 | 64 (7) | 90 (60) | 1.9 (2.5) |
| 13 | $C_{12}H_{25}CH=CH_2$ | 6 | 45 (8) | 85 (55) | 1.6 (2.5) |
| 14 | cyclohexyl-CH=CH$_2$ | 2 | 100 (34) | 100 (100) | 3.8 (9) |
| 15 | cyclohexenyl-CH=CH$_2$ | 1.5 | 100 (40) | 100 (100) | 3.3 (10) |
| 16 | phenyl-CH=CH$_2$ (styrene) | 2 | 100 (65) | 100 (100) | 0.09 (0.13) |
| 17 | 4-methylphenyl-CH=CH$_2$ | 4 | 100 (48) | 100 (100) | 0.1 (0.15) |
| 18 | 2,4-dimethylphenyl-CH=CH$_2$ | 12 | 100 (32) | 100 (100) | 0.21 (0.38) |
| 19 | $CH_3-C(=O)-O-$phenyl$-CH=CH_2$ | 0.75 | 100 (70) | 100 (100) | 0.09 (0.12) |
| 20 | phenyl-$CH_2-CH=CH_2$ | 2 | 100 (49) | 99 (99) | 1.9 (2.8) |
| 21 | phenyl-$(CH_2)_2-CH=CH_2$ | 1.5 | 100 (39) | 99 (95) | 1.4 (3) |
| 22 | phenyl-$CH=CH-CH_3$ | 6 | 10 (2) | 100 (100) | 0.07 (0.09) |

In Example 15, the internal double bond is not formylated.

The results represented in Table 2 clearly show the very favorable effect of dimethyl-β-cyclodextrin on the degree of conversion of the olefin.

Examples 23 to 26

These examples illustrate the hydroformylation of methyl undecenoate in the presence of dimethyl-β-cyclodextrin.

Methyl undecenoate, which is a raw material in the synthesis of Nylon 11, is obtained industrially from a natural product, castor oil, and more particularly by pyrolysis of methyl ricinoleate. By hydroformylation, methyl undecenoate gives 10-formyl undecanoate which, on oxidation or reductive amination, may lead respectively to 1,12-dodecanedioic acid, which is the precursor of Nylon 6-12, or to α,Ω-amino-dodecanoic acid, which is the precursor of Nylon 12.

Methyl undecenoate

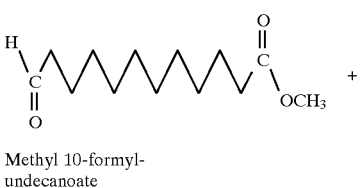

Methyl 10-formyl-undecanoate

+

-continued

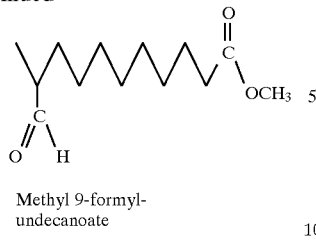

Methyl 9-formyl-
undecanoate

Example 23 illustrates the hydroformylation of methyl undecenoate, which was carried out under the following conditions.

11 ml of an aqueous solution containing 10.3 mg of Rh(acac) (CO)$_2$ (4×10$^{-2}$ mmol), 107 mg of TPPTS (0.2 mmol) and 0.56 mmol of dimethyl-β-cyclodextrin were introduced into a 25 ml autoclave. The organic phase, consisting exclusively of methyl undecenoate (4 g, 20 mmol), was then added. The autoclave was then placed under a pressure of 50 bar of a CO/H$_2$ mixture, heated to 80° C. and stirred (1500 rev/min).

Example 24 is a comparative test carried out under the same conditions as in Example 23, but without adding dimethyl-β-cyclodextrin.

Examples 25 and 26 were performed under the same conditions as in Example 23, but modifying the phosphorus/rhodium ratio, the pressure and the temperature.

The reaction conditions and the results obtained are collated in Table 3.

The degree of conversion of the olefin was determined after reaction for 5 hours.

TABLE 3

| Example | 23 | 24 | 25 | 26 |
|---|---|---|---|---|
| Phosphorus/rhodium ratio | 5 | 5 | 15 | 15 |
| Pressure (bar) | 50 | 50 | 50 | 70 |
| Temperature (°C.) | 80 | 80 | 80 | 100 |
| Conversion | 100 | 6 | 75 | 100 |
| Selectivity | 99 | 99 | 100 | 95 |
| Linear aldehydes/ branched aldehydes ratio | 1.75 | 4.14 | 2.22 | 2.04 |

The conversion, the selectivity and the linear aldehydes/branched aldehydes ratio have the meaning given previously.

Example 27

This example was carried out under experimental conditions similar to those of Example 23, but in the presence of heptane which is indispensable for dissolving the olefin used, vinylnaphthalene. The reaction was carried out in a 25 ml autoclave. The aqueous phase, having a volume of 9 ml, contained 5.2 mg (2.0×10$^{-5}$ mol) of Rh(acac) (CO)$_2$ with a TPPTS/Rh ratio=5, a dimethyl-β-cyclodextrin/rhodium ratio=14. The organic phase had a volume of 6 ml. The ratio of the olefin to rhodium was 500, the temperature was 80° C., the pressure (CO/H$_2$) was 50 bar. The results are indicated in Table 4 below.

Example 28

This example was carried out under experimental conditions similar to those of Example 1, using 2-ethylhexyl acrylate as functionalized olefin, in the presence of toluene. The reaction was carried out in a 100 ml autoclave. The aqueous phase, having a volume of 30 ml, contained 51.8 mg (0.2×10$^{-3}$ mol) of Rh(acac) (CO)$_2$ with a TPPTS/Rh ratio=10, a dimethyl-β-cyclodextrin/rhodium ratio=14. The organic phase had a volume of 40 ml. The olefin/rhodium ratio was 500, the temperature was 50° C., the pressure (CO/H$_2$) was 50 bar. The results are indicated in Table 4 below.

TABLE 4

| Example | Olefin | Duration | Conv. | Selec. | Lin./Branched |
|---|---|---|---|---|---|
| 27 |  | 6 | 85 (14) | 100 (100) | 0.1 (0.16) |
| 28 |  | 3 | 100 (5) | 97 (97) | 0.0107 (0.017) |

We claim:

1. A process for the hydroformylation of an olefin by a CO/H$_2$ gas mixture in a two-phase medium, comprising the steps of:
    placing in contact (i) an aqueous solution containing a catalytic system comprising a water-soluble transition metal complex and a water-soluble phosphine, and (ii) an olefin to form a reaction mixture,
    heating the reaction mixture obtained with stirring, after it has been placed under a pressure of the CO/H$_2$ gas mixture,
    introducing a modified cyclodextrin into the aqueous solution containing the catalytic system, said modified cyclodextrin comprising α-cyclo-dextrins, β-cyclodextrins or γ-cyclodextrins including, respectively 6, 7 or 8 glucose units and bearing one or more substituents, which may be identical or different, comprising alkyl radicals which may or may not be functionalized, hydroxyalkyl radicals, carboxyl, carboxylate, nitro, amino, sulfonate, sulfate, phosphate, ether, polyether and ammonium radicals or radicals comprising an ester function.

2. The process as claimed in claim 1, wherein the alkyl radical is a linear or branched alkyl radical having from 1 to 20 carbon atoms.

3. The process as claimed in claim 1, wherein the hydroxylalkyl radical has from 1 to 20 carbon atoms.

4. The process as claimed in claim 1, wherein the radical containing an ester function has from 1 to 20 carbon atoms.

5. The process as claimed in claim 1, wherein the modified cyclodextrin is in a form polymerized with epichlorohydrin.

6. The process as claimed in claim 1, wherein a mixture of modified cyclodextrins is introduced into the aqueous solution containing the catalytic system.

7. The process as claimed in claim 1, wherein the olefin is a linear or branched alkene.

8. The process as claimed in claim 7, wherein the olefin is a linear alkene having from 8 to 30 carbon atoms.

9. The process as claimed in claim 1, wherein the olefin is a functionalized olefin comprising a linear or branched alkene having a bulk which is less than an entry diameter of the cyclodextrin used and in which at least one of the carbon atoms of the ethylenic double bond bears at least one of:

saturated or unsaturated alicyclic radicals;

linear or branched alkenyl radicals;

aromatic radicals comprising one or more non-condensed aromatic rings which may be unsubstituted or substituted with an alkyl radical or with a functional group;

aromatic radicals comprising one or more condensed aromatic rings, which may be unsubstituted or substituted with an alkyl radical or with a functional group;

alkyl radicals bearing an aryl substitutent or a functional group; and ester functions and acyloxy functions.

10. The process as claimed in claim 9, wherein the functional group is a nitrile function, a ketone function, an acetal function or a hydroxyl function.

11. The process as claimed in claim 9, wherein, in the functionalized olefin, the carbon-carbon double bond bears at least one hydrogen atom.

12. The process as claimed in claim 11, wherein, in the functionalized olefin, the carbon-carbon double bond bears three hydrogen atoms.

13. The process as claimed in claim 1, which is carried out for a mixture of olefins.

14. The process as claimed in claim 1, wherein the catalyst is a complex of a transition metal comprising rhodium, ruthenium, palladium, iridium, cobalt, platinum, a platinum/tin couple or a platinum/iron couple, with a water-soluble phosphorus ligand.

15. The process as claimed in claim 14, wherein the catalyst is a complex of rhodium or of cobalt.

16. The process as claimed in claim 15, wherein the catalyst is $Rh_6(CO)_{16}$, $Rh_4(CO)_{12}$, $HRhCO(PR_3)_3$ or $RhCl(PR_3)_3$ wherein R represents an aryl sulfone group, $Rh(acac)(CO)_2$ wherein acac represents an acetylacetonate radical, $Rh_2Cl_2(CO)_4$, rhodium oxides ($Rh_2O_3$) or rhodium salts.

17. The process as claimed in claim 1, wherein the water-soluble phosphine is:

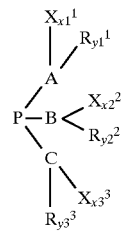

or

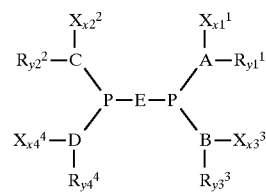

in which:

A, B, C and, if necessary, D, which may be identical or different, each represent an aryl group chosen from phenyl groups and naphthyl groups, or alkyl groups having from 1 to 10 carbon atoms;

if necessary E represents a linear or branched alkyl chain containing from 1 to 10 carbon atoms or a chain containing one or more substituted or unsubstituted phenyl groups, or a cycloalkane optionally comprising linear or branched alkyl substituents having from 1 to 6 carbon atoms;

the substituents $R^1$, $R^2$, $R^3$ and, if necessary, $R^4$, which may be identical or different, each represent hydrogen, alkyl radicals having from 1 to 4 carbon atoms, alkoxy radicals having from 1 to 4 carbon atoms, halogen atoms, —CN, —NO$_2$, —OH or —N($Z^1$)($Z^2$) groups, $Z^1$ and $Z^2$, which may be identical or different, each representing an alkyl radical having from 1 to 5 carbon atoms;

the substituents $X^1$, $X^2$, $X^3$ and, if necessary, $X^4$, which may be identical or different, each represent a carboxylic acid group, a sulfonic acid group or salts thereof, when $X^1$, $X^2$, $X^3$ and, if necessary, $X^4$ represent a carboxylic or sulfonic acid salt, the cation is an alkali-metal or alkaline-earth metal cation or an ammonium cation of formula $N(T1T^2T3T4)^+$ in which $T^1$, $T^2$, $T^3$ and $T^4$, which may be identical or different, each represent an alkyl group containing from 1 to 4 carbon atoms;

x1, x2, x3 and, if necessary x4 are identical or different numbers, ranging between 0 and 3 inclusive, at least one of them being greater than or equal to 1;

y1, y2, y3 and, if necessary, y4 are identical or different numbers, ranging between 2 and 5 inclusive.

18. The process as claimed in claim 1, wherein the phosphine/catalyst molar ratio is between 1 and 100.

19. The process as claimed in claim 1, wherein the modified cyclodextrin/catalyst molar ratio is between 1 and 100.

20. The process as claimed in claim 1, wherein the reaction temperature is between 20° C. and 200° C.

21. The process as claimed in claim 1, wherein the pressure is between 1 and 300 bar, with a partial pressure of carbon monoxide of between 0.5 and 95 bar.

22. The process as claimed in claim 1, wherein the reaction is carried out in the presence of an organic solvent that is immiscible with the aqueous phase.

23. The process as claimed in claim 1, wherein the reaction is carried out in the presence of a polar solvent that is immiscible with the organic phase.

24. The process as claimed in claim 3, wherein the hydroxylalkyl radical has from 1 to 5 carbon atoms.

25. The process as claimed in claim 4, wherein the radical containing an ester function has from 1 to 5 carbon atoms.

26. The process as claimed in claim 7, wherein said linear or branched alkene has a single carbon-carbon double bond.

27. The process as claimed in claim 26, wherein the single carbon-carbon double bond of said linear or branched alkene is in the end position.

28. The process as claimed in claim 7, wherein said olefin has more than one double bond.

29. The process as claimed in claim 9, wherein the saturated or unsaturated alicyclic radicals have from 6 to 30 carbon atoms.

30. The process as claimed in claim 9 wherein the linear or branched alkenyl radicals have from 2 to 30 carbon atoms.

31. The process as claimed in claim 9 wherein the aromatic rings are substituted with functional group which is a naphthyl radical optionally bearing one or more alkyl substituents having from 1 to 3 carbon atoms.

32. The process as claimed in claim 11, wherein, in the functionalized olefin, the carbon-carbon double bond bears at least two hydrogen atoms.

33. The process as claimed in claim 16, wherein the aryl sulfone group is a phenyl sulfone group.

34. The process as claimed in claim 16, wherein the rhodium salts are $RhCl_3$ or $Rh(OAc)_3$.

35. The process as claimed in claim 18, wherein the phosphine/catalyst molar ratio is between 2 and 20.

36. The process as claimed in claim 19, wherein the modified cyclodextrin/catalyst molar ratio is between 2 and 20.

37. The process as claimed in claim 1, wherein the olefin is an alkene represented by the formula $C_nH_{2n}$ in which n is an integer less than or equal to 30, or a functionalized olefin.

* * * * *